United States Patent
Hartoumbekis et al.

(10) Patent No.: US 9,078,694 B2
(45) Date of Patent: Jul. 14, 2015

(54) SURGICAL INSTRUMENT CLEANING ARRANGEMENT

(75) Inventors: Elias Hartoumbekis, New Haven, CT (US); Brian Rockrohr, Waterbury, CT (US); Gregory Fischvogt, Hamden, CT (US)

(73) Assignee: Covidien LP, Mansfield, MA (US)

(*) Notice: Subject to any disclaimer, the term of this patent is extended or adjusted under 35 U.S.C. 154(b) by 4 days.

(21) Appl. No.: 13/586,971

(22) Filed: Aug. 16, 2012

(65) Prior Publication Data

US 2013/0041230 A1 Feb. 14, 2013

Related U.S. Application Data

(62) Division of application No. 12/961,543, filed on Dec. 7, 2010, now Pat. No. 8,267,896.

(60) Provisional application No. 61/287,894, filed on Dec. 18, 2009.

(51) Int. Cl.
*A61M 5/178* (2006.01)
*A61B 17/34* (2006.01)
*A61B 1/12* (2006.01)

(52) U.S. Cl.
CPC .............. *A61B 17/3421* (2013.01); *A61B 1/126* (2013.01); *A61B 17/3474* (2013.01)

(58) Field of Classification Search
CPC .............. A61B 19/34; A61B 2019/343; A61B 1/00142; A61B 1/12; A61B 1/121; A61B 1/122; A61B 17/3421; A61B 17/3474; A61B 1/126; A61B 17/3462; A61B 17/3498; A61M 39/16; A61M 39/0606; A61L 2202/24; B08B 9/023
USPC ...................................................... 604/167.01
See application file for complete search history.

(56) References Cited

U.S. PATENT DOCUMENTS

| | | |
|---|---|---|
| 3,903,877 A | 9/1975 | Terada |
| 4,281,646 A | 8/1981 | Kinoshita |
| 4,497,550 A | 2/1985 | Ouchi et al. |
| 4,765,314 A | 8/1988 | Kolditz et al. |
| 4,860,731 A | 8/1989 | Matsuura |
| 4,919,113 A | 4/1990 | Sakamoto et al. |
| 4,973,321 A | 11/1990 | Michelson |
| 4,974,580 A | 12/1990 | Anapliotis |
| 4,991,565 A | 2/1991 | Takahashi et al. |
| 5,167,220 A | 12/1992 | Brown |

(Continued)

FOREIGN PATENT DOCUMENTS

| | | |
|---|---|---|
| DE | 27 45 015 A1 | 4/1978 |
| EP | 2111782 | 10/2009 |

OTHER PUBLICATIONS

European Search Report for EP10252139, dated Apr. 19, 2011 (2 pages).

*Primary Examiner* — Jason Flick

(57) ABSTRACT

An instrument cleaning apparatus facilitates the cleaning of a scope utilized during a surgical procedure. The instrument cleaning apparatus includes a base portion and a fluid retention portion. The base portion includes a substantially tubular wall having a proximal end and a distal end and a longitudinal passageway extending therethrough. The fluid retention portion is in mechanical cooperation with the base portion and is adapted to retain a cleaning fluid therein. The fluid retention portion may be contacted by the scope.

20 Claims, 3 Drawing Sheets

(56) References Cited

U.S. PATENT DOCUMENTS

| | | |
|---|---|---|
| 5,207,213 A | 5/1993 | Auhll et al. |
| 5,274,874 A | 1/1994 | Cercone et al. |
| 5,313,934 A | 5/1994 | Wiita et al. |
| 5,375,589 A | 12/1994 | Bhatta |
| 5,382,297 A * | 1/1995 | Valentine et al. ............... 134/15 |
| 5,392,766 A | 2/1995 | Masterson et al. |
| 5,400,767 A | 3/1995 | Murdoch |
| 5,413,092 A | 5/1995 | Williams, III et al. |
| 5,448,990 A | 9/1995 | De Faria-Correa |
| 5,458,633 A | 10/1995 | Bailey |
| 5,464,008 A | 11/1995 | Kim |
| 5,514,084 A | 5/1996 | Fisher |
| 5,536,236 A | 7/1996 | Yabe et al. |
| 5,538,496 A | 7/1996 | Yabe et al. |
| 5,575,756 A | 11/1996 | Karasawa et al. |
| 5,630,795 A | 5/1997 | Kuramoto et al. |
| 5,637,075 A | 6/1997 | Kikawada |
| 5,647,840 A | 7/1997 | D'Amelio et al. |
| 5,651,757 A | 7/1997 | Meckstroth |
| 5,902,413 A | 5/1999 | Puszko et al. |
| 5,989,183 A | 11/1999 | Reisdorf et al. |
| 6,096,026 A | 8/2000 | Schultz |
| 6,110,103 A | 8/2000 | Donofrio |
| 6,110,259 A | 8/2000 | Schultz et al. |
| 6,126,592 A | 10/2000 | Proch et al. |
| 6,235,008 B1 | 5/2001 | Heinzelman et al. |
| 6,299,592 B1 | 10/2001 | Zander |
| 6,354,992 B1 | 3/2002 | Kato |
| 6,421,127 B1 | 7/2002 | McAndrew et al. |
| 6,447,446 B1 | 9/2002 | Smith et al. |
| 6,589,316 B1 | 7/2003 | Schultz et al. |
| 6,699,185 B2 | 3/2004 | Gminder et al. |
| 6,702,738 B2 | 3/2004 | Ito |
| 6,712,479 B1 | 3/2004 | Seitzinger et al. |
| 6,881,236 B2 | 4/2005 | Schultz et al. |
| 7,258,712 B2 | 8/2007 | Schultz et al. |
| 7,341,556 B2 | 3/2008 | Shalman |
| 2006/0020165 A1 | 1/2006 | Adams |
| 2008/0086074 A1 | 4/2008 | Taylor et al. |
| 2009/0221872 A1 * | 9/2009 | Liddle et al. .................. 600/121 |

* cited by examiner

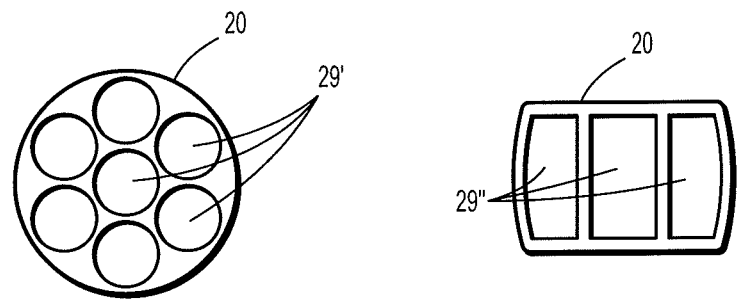
FIG. 4A  FIG. 4B
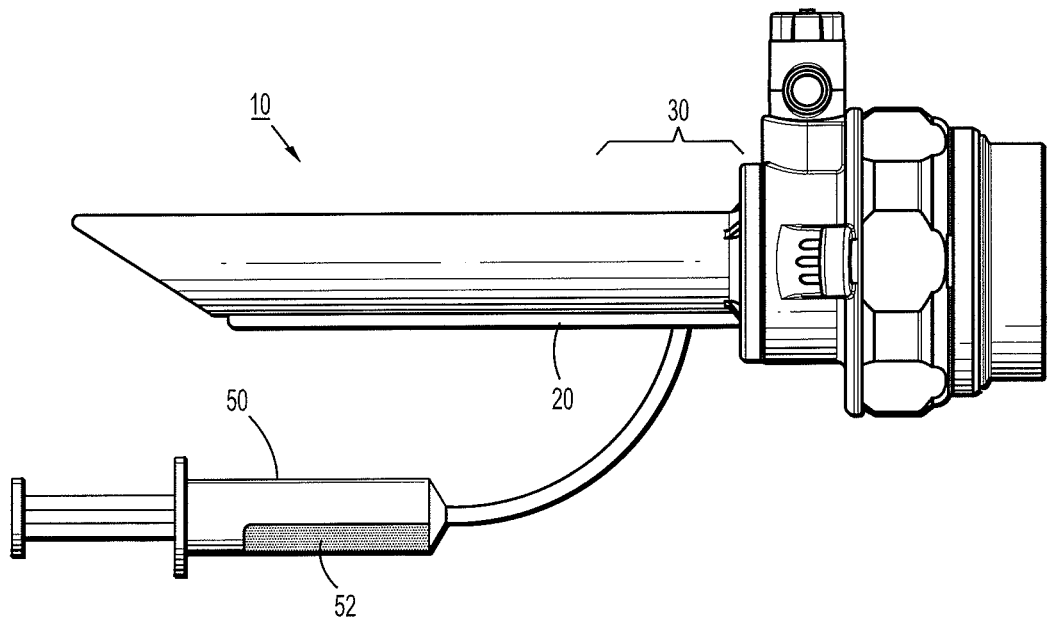
FIG. 5

SURGICAL INSTRUMENT CLEANING ARRANGEMENT

CROSS REFERENCE TO RELATED APPLICATION

The present application is a divisional application of U.S. Ser. No. 12/961,543, filed Dec. 7, 2010 now U.S. Pat. No. 8,267,896, which claims the benefit of and priority to U.S. Provisional Application Ser. No. 61/287,894 filed on Dec. 18, 2009, the entire contents of which are incorporated herein by reference.

BACKGROUND

1. Field of the Disclosure

The present disclosure relates to surgical devices and, more particularly, relates to an instrument cleaner adapted for cleaning an instrument while the instrument is within a sealed surgical portal apparatus during a minimally invasive, e.g., a laparoscopic, surgical procedure.

2. Description of the Related Art

Minimally invasive surgical procedures, including both endoscopic and laparoscopic procedures, permit surgery to be performed on organs, tissues and vessels far removed from an opening within the tissue. Laparoscopic and endoscopic procedures generally require that any instrumentation inserted into the body be sealed, e.g., provisions may be made to ensure that gases do not enter or exit the body through the incision as, for example, in surgical procedures in which the surgical region is insufflated. Particularly, a viewing scope may be introduced into the body through a sealed portal, such as a cannula, in order for the surgeon to view the region being treated on a video monitor and to see any of a variety of surgical instruments introduced either directly or through other portals into the surgical region.

In procedures that employ the internal introduction of a scope, lens smudging and/or other visual obstructions, such as fogging, can occur to obscure the surgeon's view. Known cleaning methods generally require that the scope be pulled completely out of the portal so that the lens can be cleaned and then re-inserted. It would be advantageous to be able to clean the lens while the scope is still inserted into the sealed portal.

SUMMARY

The present disclosure relates to an instrument cleaning apparatus which facilitates the cleaning of a scope inserted through a sealed portal during a surgical procedure by providing a cleaning arrangement, e.g., a cleaning solution, within the operating cavity so that the surgical instrument need not be removed therefrom.

In an embodiment, a surgical access device is provided with a housing, a sleeve extending distally from the housing, and a conduit disposed in mechanical cooperation with the sleeve. The sleeve defines a longitudinal axis and is dimensioned for passage through a tissue tract. The sleeve also defines a longitudinal bore for reception and passage of a surgical instrument. The conduit has a first portion configured to receive a fluid and a second portion configured to discharge the fluid. The second portion of the conduit is in mechanical cooperation with the sleeve.

The second portion of the conduit may be configured as a nozzle. In embodiments, the second portion of the conduit is configured as a proximally facing nozzle. The elongated portion of the conduit, positioned between the first and second portions, may be disposed adjacent to the sleeve. In other embodiments, the elongated portion is disposed within a wall of the sleeve.

Methods of using and cleaning a surgical instrument with the surgical access device are also disclosed. In accordance with the present methods, a trocar assembly is provided having a conduit operably coupled to a sleeve of the trocar assembly. The conduit includes a first portion for receiving a fluid and a second portion for discharging the fluid. The fluid may be passed from a fluid source into the first portion of the conduit. A surgical instrument is inserted through the trocar assembly to access a surgical site where a surgical function may be performed with the surgical instrument. Fluid is discharged from the second portion of the conduit to contact a distal-end of the surgical instrument.

In another embodiment, an instrument cleaning apparatus includes a base portion and a fluid retention portion. The base portion is adapted for positioning on a surgical instrument and includes a substantially tubular wall having a proximal end and a distal end and a longitudinal passageway extending therethrough. The fluid retention portion is in mechanical cooperation with the base portion and is adapted to retain a cleaning fluid therein.

BRIEF DESCRIPTION OF THE DRAWINGS

Embodiments of the present disclosure will be better appreciated by reference to the drawings wherein:

FIGS. 4A and 4B are transverse cross-sectional views of embodiments of the conduit of the surgical access device of FIGS. 1-3;

FIG. 5 is a side view of a surgical access device of FIG. 1 coupled to a fluid source in accordance with the principles of the present disclosure;

DETAILED DESCRIPTION OF THE EMBODIMENTS

The scope cleaner of the present disclosure facilitates the cleaning of a scope inserted through a sealed portal during a surgical procedure by providing a cleaning solution within the operating cavity so that the surgical instrument doesn't have to be removed therefrom. In embodiments, the sleeve of a portal apparatus includes a conduit for dispensing the cleaning solution onto the lens of the scope. In other embodiments, the cleaning solution is pre-disposed on a detachable apparatus which may be fastened to an external surface of a surgical instrument upon which a scope may be contacted and cleaned. In other embodiments, the cleaning solution is predisposed on an apparatus which is integrally formed onto an external surface of a surgical instrument upon which a scope may be contacted and cleaned. In still other embodiments, the cleaning arrangement includes a detachable or undetachable absorbent apparatus which may be fastened to, or which is integrally formed with, an external surface of a surgical instrument upon which a scope may be contacted and cleaned, e.g., by the absorbent material absorbing any fluids, fog, etc., that is disposed on the scope.

While the device according to the present disclosure is especially suitable for cleaning surgical scopes, it is envisioned that the device can be used in connection with the cleaning of other surgical instruments which are introduced through a surgical portal. Examples of surgical instrumentation which may be introduced through the portal include clip appliers, graspers, dissectors, retractors, staplers, laser probes, photographic devices, tubes, electrosurgical cutting, coagulating, and ablation devices, and other tools within the purview of those skilled in the art.

Figure 1:
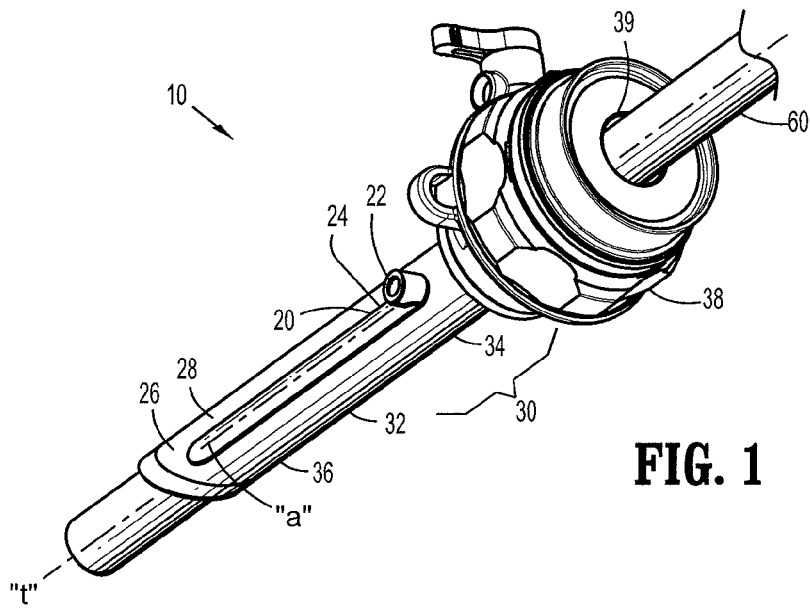
FIG. 1 is a perspective view of a surgical access device in the form of a portal and conduit in accordance with the principles of the present disclosure.
Figure 2:
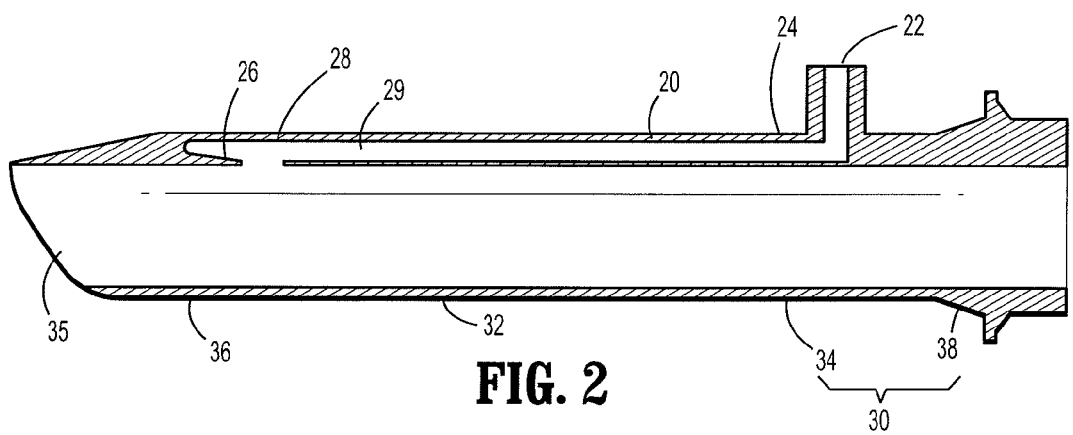
FIG. 2 is a longitudinal cross-sectional view of an alternate embodiment of the surgical access device of FIG. 1 having a conduit incorporated into a sleeve of a portal.
Figure 3:
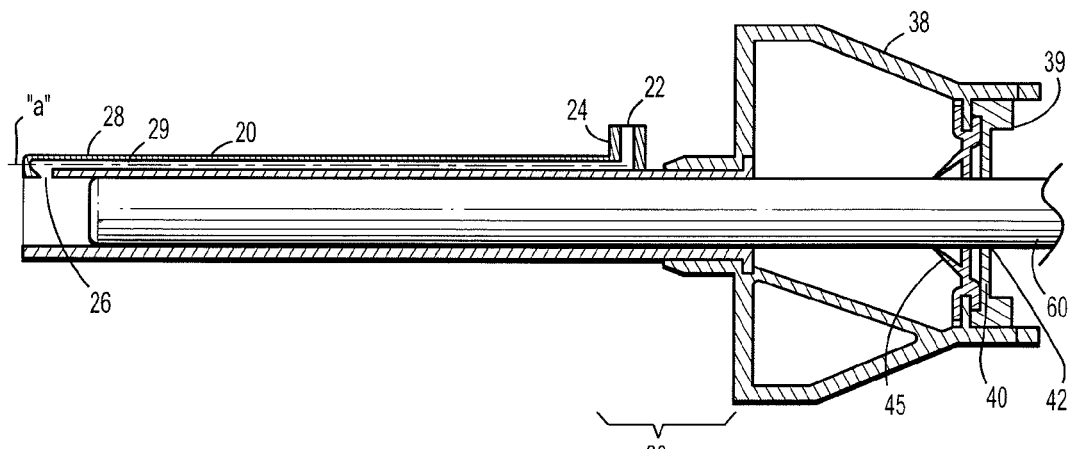
FIG. 3 is a longitudinal cross-sectional view of another embodiment of the surgical access device of FIG. 1 having a conduit adjacent a sleeve of a portal.

Referring now to the drawings, in which like reference numerals identify identical or substantially similar parts throughout the several views, FIG. 1, in conjunction with FIGS. 2 and 3, illustrate an embodiment of the scope cleaner of the present disclosure. Surgical access device 10 of the present disclosure incorporates conduit 20 with portal 30. Portal 30 may be any device suitable for the intended purpose of accessing a body cavity, such as a trocar or cannula assembly, through a tissue tract.

Portal 30 may be used in a variety of surgical applications and is particularly adapted for use in laparoscopic surgery where the peritoneal cavity is insufflated with a suitable gas, e.g., $CO_2$, to raise the cavity wall from the internal organs therein. Portal 30 is typically used with an obturator assembly (not shown) which may be a blunt, a non-bladed, or a sharp pointed instrument positionable within the passageway of portal 30. The obturator assembly is utilized to penetrate the abdominal wall or introduce portal 30 through the abdominal wall, and then subsequently is removed from portal 30 to permit introduction of scope 60 utilized to perform the procedure through the passageway.

The scope 60 may be any of a variety of laparoscopes and endoscopes, such as, for example, arthroscopes, thoracoscopes, bronchioscopes, hysteroscopes, choledochoscopes, cystoscopes, restectoscopes, and the like, depending on the surgical procedure being performed.

Portal 30 includes sleeve 32 having proximal (or leading) and distal (or trailing) ends 34 and 36, respectively, and housing 38 mounted to proximal end 34 of sleeve 32. Sleeve 32 defines a longitudinal axis "t" extending along the length of sleeve 32 and defines an internal longitudinal bore or passage 35 dimensioned to permit passage of scope 60.

Housing 38 includes central aperture 39 arranged about axis "t" and seal assembly 40. Central aperture 39 is configured and dimensioned to permit entry of scope 60. Seal assembly 40 defines a seal assembly opening 42 within seal 45, seal assembly opening 42 being in general alignment with the central aperture 39 of housing 38. Seal assembly opening 42 is configured and dimensioned such that insertion of scope 60 into seal assembly opening 42 causes the material defining seal 45 to engage the outer surface of scope 60 in a substantially fluid tight manner to minimize the formation of gaps around scope 60 and prevent gases from escaping.

In embodiments seal assembly opening 42 may include a slit which is adapted to close in the absence of a surgical object and/or in response to insufflation gases of the pressurized cavity. It is also envisioned that seal 45 of seal assembly 40 may be fabricated from a relatively rigid biocompatible polymeric material or alternatively, from a resilient and/or flexible material such as a fabric, foam, elastomeric material, or combinations thereof in order to bend or deform about an inserted scope 60 while absorbing off-axis motion.

Conduit 20 is operably coupled to portal 30. Conduit 20 may be joined with any part of sleeve 32, including its inner or outer surface as illustrated in FIGS. 2 and 3, respectively. Conduit 20 includes opening 22 on proximal end 24 and nozzle 26 on distal end 28. Conduit 20 defines a longitudinal axis "a", as shown in FIG. 3, extending along the length of conduit 20 and defines an internal longitudinal channel 29 dimensioned to permit the flow of fluid therethrough. In embodiments, longitudinal axis "a" may be substantially parallel to axis "t" of sleeve 32.

The size and dimension of channel 29 of conduit 20 may vary. In embodiments, channel 29 may be uniform in size and diameter along the length of conduit 20. A change or decrease, however, in the surface area of channel 29 may aid in discharging fluid through nozzle 26. Therefore, in other embodiments, channel 29 may taper towards distal end 28 of conduit 20. It is also envisioned that channel 29 may be comprised of smaller channels 29' and 29" as illustrated in FIGS. 4A and 4B, respectively. By decreasing the diameter of channel 29 through which fluid may flow, the resistance of the fluid increases. Pressure is thereby built up for the discharge of the fluid through nozzle 26.

Proximal opening 22 of conduit 20 is configured to connect to fluid source 50. Opening 22 and fluid source 50 may be connected by tubing or other means as is within the purview of those skilled in the art. Fluid source 50 may be a syringe as illustrated in FIG. 5. Fluid source 50 may include syringes, pumps, valves, and the like which may be pressurized or un-pressurized. Nozzle 26 opens into distal end 36 of longitudinal passage 35 of sleeve 32 of portal 30. Nozzle 26 may be a spigot, spout, or any other opening for discharging and/or spraying fluid 52 received by opening 22 from fluid source 50. It is envisioned that nozzle 26 faces proximally, such that at least a portion of the projected spray of fluid 52 from nozzle 26 is proximal to the distal-most end of sleeve 32.

Nozzle 26 may include one or more openings or include a series or pattern of openings conducive to applying and washing surgical instrumentation 60. In embodiments, nozzle 26 may evenly distribute fluid 52 across a predetermined area or focus fluid 52 into one or more regions. In embodiments, nozzle 26 may include openings of varying sizes and/or angles in order to provide additional resistance to fluid 52 for a more forceful or jet-like flow of fluid 52 or to direct flow of fluid 52.

Fluid 52 may be a washing or rinsing fluid such as saline or sterile water. Fluid 52 may be an anti-fogging solution or may be warmed to reduce the likelihood of fogging. Defogging solutions may be water, glycol, and water soluble wetting agents. In embodiments, fluid 52 is commercially available surgical anti-fog solution FRED™ available from Covidien (Mansfield, Mass.). Fluid 52 may contain a biocompatible cleaning agent or a bioactive agent that has clinical use.

Surgical access device 10 may be a single monolithically formed unit or composed of several components connected to each other through conventional means including a bayonet coupling, a threaded connection, snap fit, ultrasonic welding or any other means envisioned by one skilled in the art including, e.g., adhesive means. Sleeve 32 and housing 38 of portal 30 may be a monolithically formed unit or may be connected to each other through conventional means as described above. In a like manner, sleeve 32 of portal 30 and conduit 20 may be monolithically formed or may be connected to each other through conventional means. Surgical access device 10, including conduit 20 and/or portal 30, may be formed of any suitable medical grade material, such as stainless steel or other rigid materials, including polymeric materials, such as polycarbonate and the like. Surgical access device 10 may be transparent, translucent, or opaque.

To use the scope cleaner in connection with the performance of a surgical task during a laparoscopic procedure, the peritoneal cavity is insufflated to establish the pneumoperitonum. Surgical access device 10 is introduced into an insufflated abdominal cavity typically utilizing a sharp or non-blade trocar obturator to access the cavity and the obturator is removed. A scope 60 is advanced through surgical access device 10 by inserting instrument 60 into central aperture 39 of housing 38 and through seal assembly 40 whereby seal assembly 40 accommodates instrument 60 in substantial scaled relation therewith. Scope 60 is distally passed through seal assembly 40, longitudinal passage 35, and into the body cavity. The desired surgical task is performed with scope 60. During manipulation of scope 60, should scope 60 fog, become soiled, accumulate debris, or obstruct the surgeon's view in any way, scope 60 is adjusted within sealed portal 30 so that the soiled part of scope 60, e.g., the lens, is substantially aligned with the projected spray of fluid 52 from nozzle 26. Fluid 52 is then passed through channel 29 of conduit 20 and out through nozzle 26 in order to spray and clean scope 60.

Figure 6:
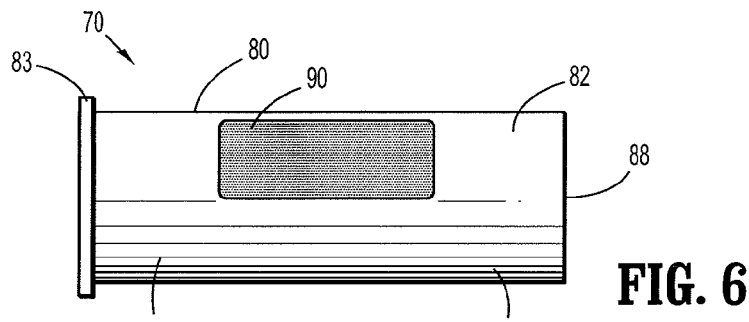
FIG. 6 is a perspective view of a scope cleaner having a base portion and fluid retention portion in accordance with the principles of the present disclosure.

Turning now to FIG. 6, the scope cleaner 70 may be an apparatus which may be detachably secured to the outer surface or shaft of a surgical instrument 62, such as the sleeve of a trocar assembly or any other instruments which are introduced into a surgical cavity during a minimally invasive surgical procedure as discussed above. In embodiments, scope cleaner 70 is attached to a surgical instrument 62 which remains in the surgical cavity for an extended period of time, such as a tissue grasping instrument.

Figure 7A:
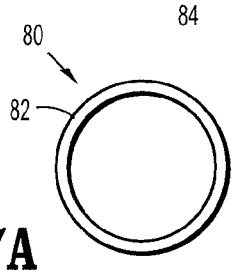
FIGS. 7A and 7B are transverse cross-sectional view of embodiments of the base portion of the scope cleaner of FIG. 6.
Figure 7B:
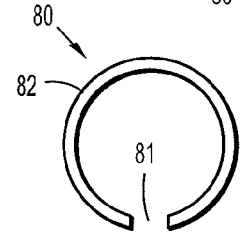

Scope cleaner 70 includes a base portion 80 and a fluid retention portion 90. Base 80 has a tubular configuration and includes wall 82. Wall 82 includes proximal end 84 and distal end 86 and defines an internal longitudinal opening 88 extending along the entire length, from the proximal end 84 to the distal end 86, of wall 82. Wall 82 may be continuous as illustrated in FIG. 7A or may have a longitudinally extending slit 81 formed therein, as illustrated in FIG. 7B.

Wall 82 may be formed from a flexible polymer and/or elastomeric material, such as, for example, polyolefins such as polypropylene and polyethylene, polyesters such as polyethylene terephthalate, polyamides such as nylon, polyurethanes, silicones, vinyl, and rubber. The flexible materials are adaptable and amendable for insertion onto a surgical instrument 62. Wall 82 must have a sufficient elasticity to bend and deform upon placement onto the shaft of surgical instrument 62 while conforming about the outer dimensioning of the surgical instrument 62. A grip or tab 83 may be added to base 80, such as at proximal end 84 as illustrated in FIG. 6, to assist in inserting the scope cleaner 70 about instrument 62. Tab 83 radially extends around and is raised from a portion of wall 82 to facilitate gripping by the hand of the holder.

In other embodiments, wall 82 is formed from a relatively rigid material, such as plastics. Plastics may be formed from polymers such as those described above. In embodiments, the wall is formed from a high density polymer and includes a longitudinally extending slit as described above to facilitate snap fitting of the scope cleaner onto a surgical instrument. It is contemplated that the scope cleaner could be assembled with the surgical instrument during manufacturing of the instrument.

Figure 8:
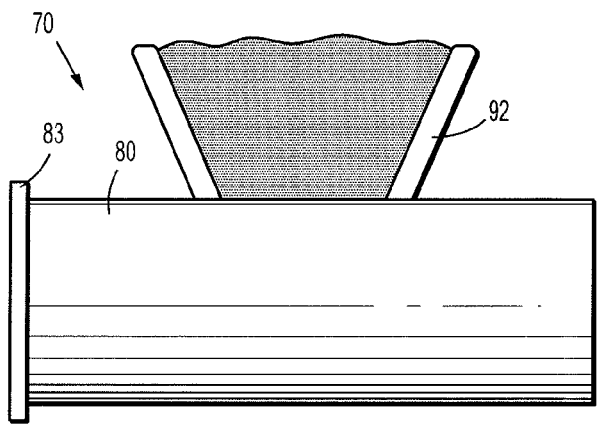
FIG. 8 is an alternate embodiment of a scope cleaner of FIG. 6.

Fluid retention portion 90 is in mechanical cooperation with base portion 80. Fluid retention portion 90 may be integrated into wall 82 of base 80 or may be attached to the outer surface of wall 82. In embodiments, the fluid retention portion is sufficiently thin so that the scope cleaner 70 maintains a substantially uniform diameter along the length thereof. As illustrated in the current embodiment, fluid retention portion 90 is a pad fastened to the surface of wall 82 by conventional coupling means, such as by the use of adhesives. In other embodiments, such as that illustrated in FIG. 8, the fluid retention portion 92 has a basket-like configuration which protrudes from the outer surface of wall 82. As illustrated in this embodiment, the portion of the scope cleaner 70 upon which the fluid retention portion 92 is retained has an extended diameter. Fluid retention portion 92 must be made of a flexible material so that is will flex during insertion and withdrawal of the instrument on which it is applied during a surgical procedure.

Fluid retention portion 90 is adapted and configured to allow for the retention of fluid 52 therein. In embodiments, fluid retention portion 90 is formed from a porous material which includes openings or pores over at least a portion of a surface thereof. Examples include meshes, foams, and sponges. In other embodiments, fluid retention portion 90 is formed from an absorbent material. The absorbent material may be any natural or synthetic cloth or felt material within the purview of those skilled in the art. A moisture wicking material that does not absorb moisture into the fiber but maintains the moisture on the surface thereof may also be used separately or in combination with a porous or absorbent material. Examples include, for example, polyester, polyester-based fabrics, nylon, spandex, and blends or combinations thereof. In embodiments, fluid retention portion 90 is fabricated from a mesh of spandex. In other embodiments, fluid retention portion 90 includes a nitinol wire frame and an absorbent material contained therein.

Figure 9:
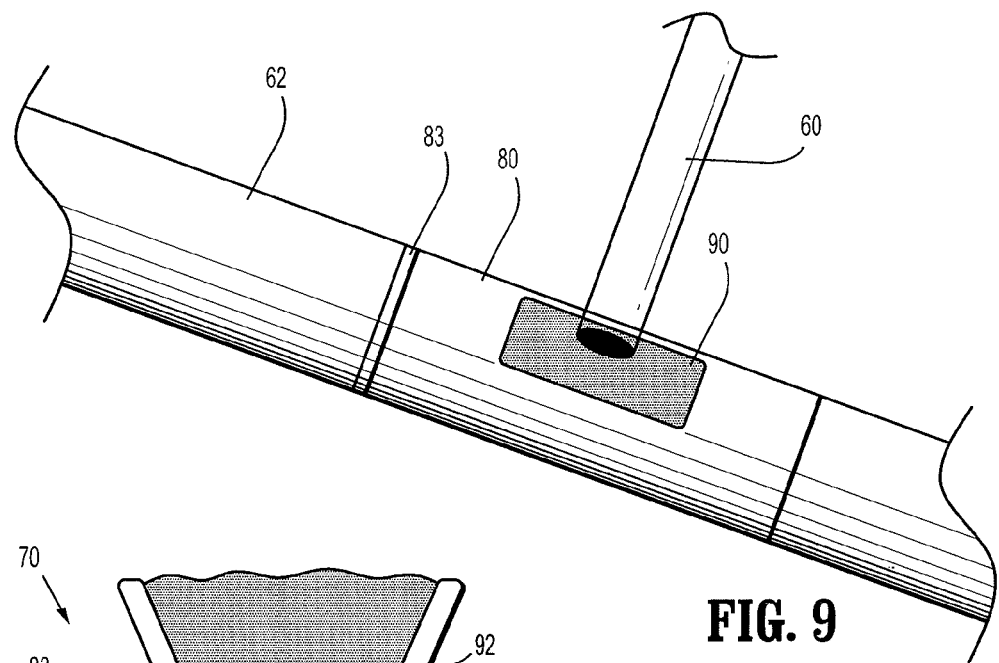
FIG. 9 is an embodiment of the scope cleaner of FIG. 6 attached to a surgical instrument.

As illustrated in FIG. 9, to use the scope cleaner 70 in connection with the performance of a surgical task during a laparoscopic procedure, scope cleaner 70 is inserted onto the shaft of instrument 62. Fluid 52, such as FRED™ anti-fog solution, is applied onto fluid retention portion 90 prior to insertion of the instrument 62 into the operating cavity. A scope 60 is also introduced into the body cavity through a separate port. The desired surgical task is performed with scope 60 and instrument 62. During manipulation of scope 60, should the scope 60 fog, become soiled, accumulate debris, or obstruct the surgeon's view in any way, scope 60 is moved in contact with fluid retention portion 90 of scope cleaner 70. With the application of light pressure, the scope 60 is moved in a clockwise/counterclockwise motion in order to clean scope 60.

It will be understood that various modifications and changes in form and detail may be made to the embodiments of the present disclosure without departing from the spirit and scope of the disclosure. Therefore, the above description should not be construed as limiting the invention but merely as exemplifications of embodiments thereof. Those skilled in the art will envision other modifications within the scope and spirit of the present disclosure as defined by the claims appended hereto.

What is claimed is:
1. An instrument cleaning apparatus comprising:
 a base portion including a substantially tubular wall having a proximal end and a distal end, the wall including a longitudinally extending slit, an outer surface and an inner surface defining a longitudinal passageway extending through the base portion, the base portion adapted for positioning on a surgical instrument; and a unitary fluid retention portion connected to and fully disposed radially outwardly from the outer surface of the wall of the base portion, an outward facing surface of the fluid retention portion configured to be contacted during a surgical procedure by a scope.

2. The instrument cleaning apparatus according to claim 1, wherein the base portion includes a tab for gripping the base portion.

3. The instrument cleaning apparatus according to claim 2, wherein the tab radially extends around and is raised from a portion of the outer surface of the wall.

4. The instrument cleaning apparatus according to claim 1, wherein the fluid retention portion comprises a porous material selected from the group consisting of meshes, foams, and sponges.

5. The instrument cleaning apparatus according to claim 1, wherein the fluid retention portion comprises an absorbent material.

6. The instrument cleaning apparatus according to claim 1, wherein the fluid retention portion comprises a fluid wicking material.

7. The instrument cleaning apparatus according to claim 1, wherein the fluid retention portion is adapted to retain a cleaning solution therein.

8. The instrument cleaning apparatus according to claim 1, wherein the fluid retention portion has a basket-like configuration.

9. The instrument cleaning apparatus according to claim 1, wherein the fluid retention portion is made of a flexible material that flexes during insertion and withdrawal of the surgical instrument during a surgical procedure.

10. The instrument cleaning apparatus according to claim 1, wherein the fluid retention portion is sufficiently thin so as to maintain a substantially uniform diameter along a length of the base portion.

11. An instrument cleaning apparatus, comprising:

a base portion including a substantially tubular wall having a proximal end and a distal end, the wall including an outer surface and an inner surface defining a longitudinal passageway extending therethrough, the base portion adapted for positioning on a surgical instrument; and a unitary fluid retention portion connected to and fully disposed radially outwardly from within the outer surface of the wall of the base portion, an outward facing surface of the fluid retention portion configured to be contacted during a surgical procedure by a scope.

12. An instrument cleaning apparatus comprising:

a base portion including a substantially tubular wall defined between a proximal end and a distal end of the base portion, the wall including an outer surface and an inner surface defining a longitudinal passageway extending through the base portion from a first opening defined in the proximal end to a second opening defined in the distal end, the base portion adapted for positioning on a first surgical instrument; and a unitary fluid retention portion connected to and fully extending radially outwardly from the wall of the base portion, an outward facing surface of the fluid retention portion configured to be contacted during a surgical procedure by a second surgical instrument.

13. The instrument cleaning apparatus according to claim 12, wherein the base portion includes a tab for gripping the base portion.

14. The instrument cleaning apparatus according to claim 13, wherein the tab radially extends around and is raised from a portion of the outer surface of the wall.

15. The instrument cleaning apparatus according to claim 12, wherein the wall of the base portion includes a longitudinally extending slit.

16. The instrument cleaning apparatus according to claim 12, wherein the fluid retention portion comprises a porous material.

17. The instrument cleaning apparatus according to claim 12, wherein the fluid retention portion comprises an absorbent material.

18. The instrument cleaning apparatus according to claim 12, wherein the fluid retention portion comprises a fluid wicking material.

19. The instrument cleaning apparatus according to claim 12, wherein the fluid retention portion is adapted to retain a cleaning solution therein.

20. The instrument cleaning apparatus according to claim 12, wherein the fluid retention portion is integrated into the wall of the base portion.

* * * * *